United States Patent
Hong

(10) Patent No.: US 10,258,431 B2
(45) Date of Patent: Apr. 16, 2019

(54) TRANSPARENT ALIGNER AND METHOD FOR MANUFACTURING SAME

(71) Applicant: Kyung Jae Hong, Seoul (KR)

(72) Inventor: Kyung Jae Hong, Seoul (KR)

( * ) Notice: Subject to any disclaimer, the term of this patent is extended or adjusted under 35 U.S.C. 154(b) by 94 days.

(21) Appl. No.: 15/505,353

(22) PCT Filed: Aug. 20, 2015

(86) PCT No.: PCT/KR2015/008720
§ 371 (c)(1),
(2) Date: Feb. 21, 2017

(87) PCT Pub. No.: WO2016/028106
PCT Pub. Date: Feb. 25, 2016

(65) Prior Publication Data
US 2017/0265967 A1 Sep. 21, 2017

(30) Foreign Application Priority Data

Aug. 22, 2014 (KR) .................. 10-2014-0110024
Aug. 22, 2014 (KR) .................. 10-2014-0110034
(Continued)

(51) Int. Cl.
*A61C 7/08* (2006.01)
*A61C 13/00* (2006.01)
(Continued)

(52) U.S. Cl.
CPC ............... *A61C 7/08* (2013.01); *A61C 7/002* (2013.01); *A61C 13/00* (2013.01); *A61C 13/34* (2013.01);
(Continued)

(58) Field of Classification Search
CPC ......... A61C 13/00; A61C 13/34; A61C 7/002; A61C 7/08; A61C 2007/004; B33Y 10/00; B33Y 80/00; B29C 51/10; B29C 64/386
See application file for complete search history.

(56) References Cited

U.S. PATENT DOCUMENTS 5,607,305 A * 3/1997 Andersson ............. A61C 9/002
433/223
5,975,893 A * 11/1999 Chishti .................... A61C 7/00
433/6
(Continued)

FOREIGN PATENT DOCUMENTS

JP WO2004/049967 6/2004
JP 2009-297525 12/2009
(Continued)

OTHER PUBLICATIONS

International Search Report dated Dec. 15, 2015 in corresponding International Application No. PCT/KR2015/008720.

*Primary Examiner* — Edward Park
(74) *Attorney, Agent, or Firm* — Antonio Ha & U.S. Patent, LLC

(57) ABSTRACT

A method for manufacturing a transparent aligner for dental alignment is disclosed. The method may include: determining a tooth contour model which includes a contour portion surrounding a surface of a tooth requiring rotational correction; determining an axis of rotation for the tooth requiring rotational correction; determining two points touching exterior surfaces of the tooth requiring rotational correction based on the axis of rotation and a direction of rotation required for correcting the tooth requiring rotational correction, the two points being symmetrical with respect to the axis of rotation; determining a rotational correction model for the rotational correction by protruding the contour por- (Continued)

tion towards a tooth surface and towards a direction of rotation at the two points; and generating the 3D dental alignment model data by applying the rotational correction model.

8 Claims, 19 Drawing Sheets

(30) Foreign Application Priority Data

| Aug. 22, 2014 | (KR) | ................ | 10-2014-0110040 |
| Aug. 22, 2014 | (KR) | ................ | 10-2014-0110047 |
| Oct. 17, 2014 | (KR) | ................ | 10-2014-0141139 |
| Oct. 17, 2014 | (KR) | ................ | 10-2014-0141140 |
| Oct. 17, 2014 | (KR) | ................ | 10-2014-0141141 |

(51) Int. Cl.
  *A61C 13/34* (2006.01)
  *B33Y 10/00* (2015.01)
  *B33Y 80/00* (2015.01)
  *A61C 7/00* (2006.01)
  *B29C 51/10* (2006.01)
  *B29C 64/386* (2017.01)

(52) U.S. Cl.
  CPC ............... *B33Y 10/00* (2014.12); *B33Y 80/00* (2014.12); *A61C 2007/004* (2013.01); *B29C 51/10* (2013.01); *B29C 64/386* (2017.08)

(56) References Cited

U.S. PATENT DOCUMENTS

| 6,217,325 | B1 | 4/2001 | Chishti et al. |
| 2010/0167243 | A1* | 7/2010 | Spiridonov .............. A61C 7/00 |
| | | | 433/224 |

FOREIGN PATENT DOCUMENTS

| KR | 10-1138354 | 4/2012 |
| KR | 10-1173548 | 8/2012 |
| KR | 10-1295612 | 8/2013 |
| KR | 10-1349356 | 1/2014 |

* cited by examiner before correction after correction

TRANSPARENT ALIGNER AND METHOD FOR MANUFACTURING SAME

TECHNICAL FIELD

The present invention relates to a dental aligner and, more particularly, to a transparent aligner and a method for manufacturing the same.

BACKGROUND ART

Dental alignment is widely being used for treating malocclusion or for cosmetic purposes. A widely used apparatus based on the related art is the so-called fixed braces, which involve affixing brackets onto the teeth and coupling wires to the brackets to pull or push the brackets for dental alignment.

In fixed braces, the brackets are usually mounted onto the smooth outer surfaces, i.e. the labial side, of the teeth. While such fixed braces provide advantages in terms of effectiveness and convenience of the procedure, patients may often be averse to using braces because of the lowered aesthetic appeal, as illustrated in FIG. 23.

In addition to the problem of fixed braces having a negative aesthetic effect, there also other problems such as the inconvenience of having the braces affixed all the time. To resolve such problems, transparent aligners (and procedures) such as Invisalign and Clear-aligner have been proposed. Both of the above are aligners having transparent forms and may be worn in the manner of a mouthpiece.

The former entails dividing the transformation process between the current state and the target state of the teeth into several dozens of stages. After molding pockets that match the dental arrangement for each stage, the patient would wear the dental pockets, replacing the pockets for each stage. The latter is similar to the former, but is differentiated in that progress is observed and the pockets are fabricated as necessary.

The procedure using transparent aligners was developed in 1997, with the launching of the dental aligner "Invisalign System" by the U.S.-based company "Align Technology, Inc." Details may be found in U.S. Pat. No. 5,975,893 and No. 6,217,325 held by the company mentioned above. The "Invisalign System" creates 20 to 30 pairs of mockups for the stages the teeth must progress through until they ultimately reach the desired positioned, using a special program to obtain a virtual simulation based on 3-dimensional scans of the patient's teeth. Afterwards, transparent plastic casts are fabricated according to each of the mockups and provided to the patient, where the plastic casts allow movement of the teeth.

The feature of the "Invisalign System" is to gradually move the misaligned teeth to their final target positions by fitting the teeth into a series of plastic casts according to the corresponding stages. Since the plastic casts are made from a transparent material and are not readily visible, they have minimal negative impact on a patient's daily social life. Another advantage is that the aligner can be easily removed and reinserted as needed by the patient.

With such transparent alignment method, an aligner of a transparent material (hereinafter referred to as a transparent aligner) is capped onto the teeth like a mouthpiece, so that it is not readily discernible from the exterior. Moreover, it can be removed and reinserted at will, allowing greater convenience. Due to these advantages, this method is gaining more popularity compared to other alignment methods.

However, although the existing transparent aligner may be great for pulling or pushing teeth, it cannot apply a strong rotating force on the teeth, so that it is ineffective for rotating correction. In particular, the concave portion at the upper part of the teeth mockup may apply a greater force on the teeth compared to other portions, making it difficult to apply rotational correction on the teeth.

Also, with the existing transparent aligner, it may not be easy to remove the aligner if the teeth are severely crooked or if the aligner is too tight, incurring problems such as broken finger nails or damaged gums.

Furthermore, the existing transparent aligner may be limited in terms of application to children or adolescents as it does not provide space for a developing permanent tooth before or after a primary tooth is shed.

Also, the existing transparent aligner has a specific thickness. Thus, when it is needed to move the teeth by a large amount or a wearer needs to wear the aligner for an extended period, the aligner may cause pain, or the aligner may not function properly due to abrasion.

DISCLOSURE

Technical Problem

The present invention has been made keeping in mind the above problems occurring in the related art, and an object of the present invention is to provide a transparent aligner and a method for manufacturing the transparent aligner, where the transparent aligner is effective at rotational correction of teeth.

Another objective of the present invention is to provide a transparent aligner and a method for manufacturing the transparent aligner, where the transparent aligner allows easy removal.

Yet another objective of the present invention is to provide a transparent aligner and a method for manufacturing the transparent aligner, where the transparent aligner provides an allowance for a permanent tooth before or after a primary tooth has been shed.

Still another objective of the present invention is to provide a transparent aligner and a method for manufacturing the transparent aligner, where the transparent aligner has different thicknesses.

Another objective of the present invention is to provide a transparent aligner and a method for manufacturing the transparent aligner, where the transparent aligner is effective for rotational correction of teeth.

Another objective of the present invention is to provide a transparent aligner and a method for manufacturing the transparent aligner, where the transparent aligner allows easy removal.

Yet another objective of the present invention is to provide a transparent aligner and a method for manufacturing the transparent aligner, where the transparent aligner provides an allowance for a permanent tooth before or after a primary tooth has been shed.

Still another objective of the present invention is to provide a transparent aligner and a method for manufacturing the transparent aligner, where the transparent aligner has different thicknesses.

Technical Solution

A method for manufacturing a transparent aligner according to an embodiment of the present invention, devised to accomplish the objectives above, may include:

providing a 3D-modeled teeth mockup; and generating 3D dental alignment model data by incorporating alignment data into the 3D-modeled teeth mockup; fabricating an alignment teeth mockup using the 3D dental alignment model data; and applying vacuum compression after placing a synthetic resin sheet on the alignment teeth mockup.

Here, generating the 3D dental alignment model data may include:

determining a tooth contour model that has a contour portion surrounding a surface of a tooth requiring rotational correction;

determining the axis of rotation for the tooth requiring rotational correction;

determining two points, which are symmetrical with respect to the axis of rotation and which touch the exterior surfaces of the tooth requiring rotational correction, based on the axis of rotation and a direction of rotation required for correcting the tooth requiring rotational correction; and determining a rotational correction model for the rotational correction by protruding the contour portion towards a tooth surface and towards a direction of rotation at the two points.

Here, it may be preferable to determine a correction model that utilizes second protrusions formed on the lingual (tongue) side wall and labial (lip) side wall of a second tooth pocket, which corresponds to a tooth that requires pulling aid, where the second protrusions push the tooth requiring pulling aid in the direction of pulling.

Before the applying of the vacuum compression, an operation of attaching an elliptical patch at an outside gum portion at a molar of the alignment teeth mockup may be performed.

Before the applying of the vacuum compression, an operation of filling in a tooth portion with resin may be performed, for a portion of the alignment teeth mockup where a primary tooth was shed and a permanent tooth has not yet developed.

In the applying of the vacuum compression, synthetic resin sheets of different thicknesses may be sequentially applied to fabricate a multiple number of transparent dental aligners.

Before the applying of the vacuum compression, it may be preferable to obtain a cover by applying a heat seal resin on the alignment teeth mockup, and then performing the vacuum compression operation with the obtained cover covering the alignment teeth mockup.

A transparent aligner according to an embodiment of the present invention is devised which can accomplish the objectives above.

The transparent aligner may be a transparent aligner of a mouthpiece type for dental alignment and may include:

an insertion aligner part, in which tooth pockets are formed corresponding to an aligned teeth arrangement, and which is configured to be fitted over a corresponding group of teeth; and a support part extending from the insertion aligner part to the gums, where at least one of the tooth pockets is a first tooth pocket corresponding to a tooth that requires rotational correction, the first tooth pocket comprises a labial side wall and a lingual side wall surrounding a labial side and a lingual side of the tooth requiring rotational correction, and protrusions may be provided on the labial side wall and the lingual side wall at symmetric positions with respect to an axis of rotation of the tooth requiring rotational correction, with the protrusions protruding towards the tooth requiring rotational correction.

Here, the protrusion may include a convex portion that protrudes towards the tooth requiring rotational correction and a concave portion that is positioned at the rear of the convex portion, and it may be preferable to have the concave portion filled with a solid support material.

Here, if the tooth requiring rotational correction were divided into an upper part and a lower part with respect to the midpoint height, it may be preferable to have the protrusions positioned at the lower part of the tooth requiring rotational correction.

The transparent aligner may further include:

a second tooth pocket corresponding to a tooth requiring pulling aid, where the second tooth pocket may include a labial side wall and a lingual side wall surrounding a labial side and a lingual side, respectively, of the tooth requiring pulling aid, and second protrusions are provided on the labial side wall and the lingual side wall, where the second protrusions are configured to push the tooth requiring pulling aid in a direction of pulling.

Also, it may be preferable for the transparent aligner to further include:

a third tooth pocket corresponding to a portion where a primary tooth was shed and a permanent tooth will develop.

Also, it may be preferable for the transparent aligner to have:

a removal handle formed at an outside gum portion at a molar of the support part.

The transparent aligner may preferably be formed such that several of the transparent aligners having different thicknesses form one set.

According to an embodiment of the present invention, a transparent aligner that is effective for rotational correction of teeth can be manufactured.

Also, a transparent aligner that can be readily removed even if the teeth are severely misaligned or the aligner is too tight can be provided.

Also, a transparent aligner that allows space for a permanent tooth to grow before or after a primary tooth is shed can be provided.

Also, a transparent aligner that does not cause pain even if the teeth are moved by a great amount or the aligner is used for an extended period can be provided.

BEST MODE

Figure 7:
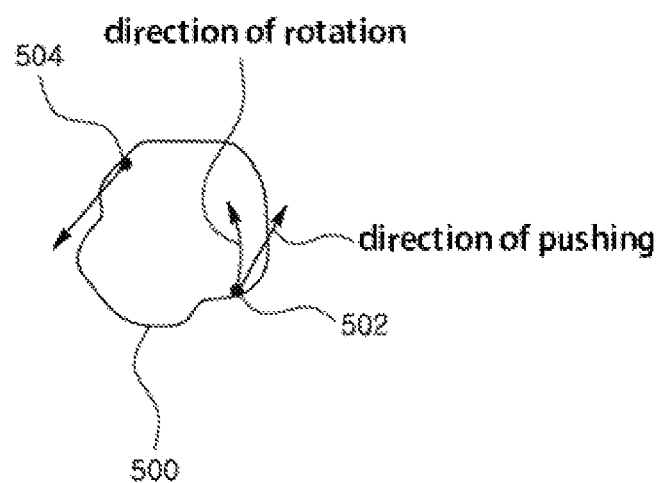
FIG. 7 illustrates a cross section of an alignment tooth model for a tooth that requires rotational correction and a corresponding first tooth pocket.
Figure 8:
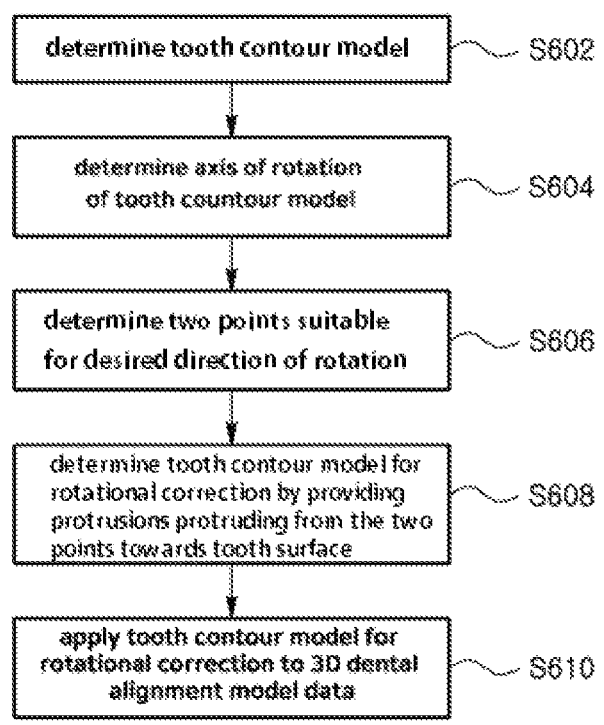
FIG. 8 is a flow diagram representing a method of determining the two points illustrated in FIG. 7.

The best mode for practicing an embodiment of the present invention is illustrated in FIG. 8, where FIG. 8 is a flow diagram representing a method of determining the two points illustrated in FIG. 7.

First, a tooth contour model may be determined, which has a contour that surrounds the surfaces of a tooth requiring rotational correction (s602).

The tooth contour model may be shaped as the tooth requiring rotational correction.

The axis of rotation for the tooth contour model may be determined (s604).

The axis of rotation may be determined in consideration of the geometrical shape of the tooth.

Based on the axis of rotation and the direction of rotation required for the correction, two correction-position points 502, 504 suitable for the desired direction of rotation may be determined (s606).

That is, two points may be determined which are symmetrical with respect to the axis of rotation and at which a force couple can be generated on the outer surfaces of the tooth.

A rotational correction model 500 may be determined for providing rotational correction by protruding the contour at the two points towards the inward side of the tooth and in the direction of rotation (s608).

The rotational correction model 500 may be incorporated into the 3D alignment teeth data (s610).

The above may be considered the best mode for manufacturing a transparent aligner.

MODE FOR INVENTION

A transparent aligner according to an embodiment of the present invention may be of a mouthpiece type and may include an insertion aligner part, in which tooth pockets are formed corresponding to an aligned teeth arrangement and which is configured to be fitted over a corresponding group of teeth, and a support part, which extends from the insertion aligner part to the gums.

The insertion aligner part may be composed of individual tooth pockets formed in a row, where a tooth pocket is a transparent cover that surrounds the lingual side and the labial side of a tooth.

In addition, a transparent aligner according to an embodiment of the present invention may include a first tooth pocket that corresponds to a tooth requiring rotational correction, a second tooth pocket that corresponds to a tooth requiring pulling aid, a third tooth pocket that corresponds to a portion where a primary tooth has been shed but a permanent tooth has not yet developed, and a handle part intended for aiding the removal of the transparent aligner.

Figure 1:
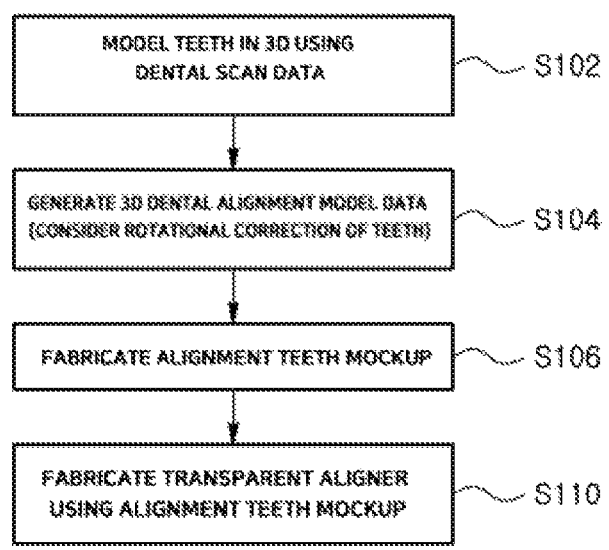
FIG. 1 is a flow diagram of a method for manufacturing a transparent aligner according to an embodiment of the present invention.

FIG. 1 is a flow diagram of a method for manufacturing a transparent aligner according to an embodiment of the present invention.

Referring to FIG. 1, a 3D-modeled teeth mockup may first be provided, using dental scan data (s102).

The 3D-modeled teeth mockup can be obtained by scanning a plaster mockup of the teeth with a 3-dimensional scanner.

Next, 3D dental alignment model data may be generated by incorporating alignment data into the 3D-modeled teeth mockup (s104).

To be more specific, the progress between the current state of the teeth and the future target state of the teeth may be divided into several dozens of stages, with the 3D dental alignment model data generated for the teeth arrangement of each stage.

The generated 3D dental alignment model data may be used in generating design information for the patient's dental aligner. Here, the design information for the dental aligner may be design information modeled with 3D CAD and may be provided to and processed by a 3D printer to manufacture a dental aligner of a corresponding form.

According to an embodiment of the present invention, the process of generating the 3D dental alignment model data may include generating 3D dental alignment model data for forming a first tooth pocket, which corresponds to a tooth that requires rotational correction, and a second tooth pocket, which corresponds to a tooth that requires pulling aid.

Figure 2:
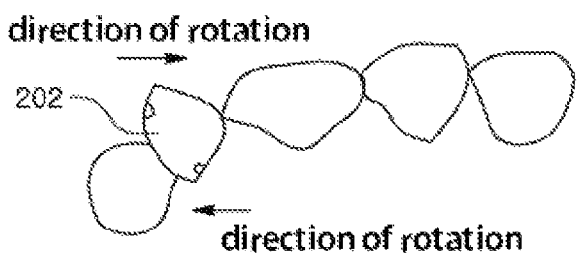
FIG. 2 illustrates an alignment method of a transparent aligner according to an embodiment of the present invention.

FIG. 2 illustrates a method for manufacturing a transparent aligner according to an embodiment of the present invention and is provided to describe a method of aligning a tooth that requires rotational correction.

Referring to FIG. 2, it can be seen that a misaligned tooth 202 requiring rotational correction can be rotated by choosing two points which are symmetrical with respect to the rotational center of the tooth and applying a force couple in the direction in which rotation is desired.

Figure 3:
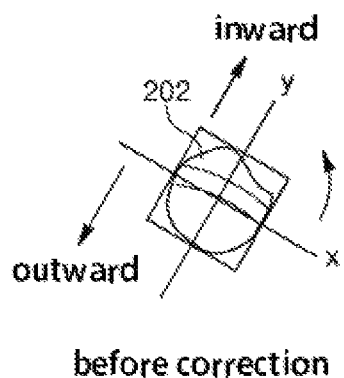
FIG. 3 is a diagram for explaining the selection of a center line in choosing a direction for rotational correction.

FIG. 3 is provided to illustrate a method of selecting the contact points for applying the rotational correction illustrated in FIG. 2.

Figure 4:
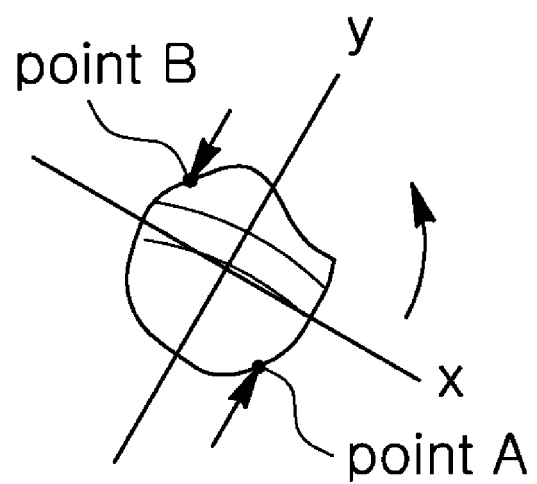
FIG. 4 is a diagram for explaining a method of choosing contact points for the rotational correction illustrated in FIG. 2.
Figure 5:
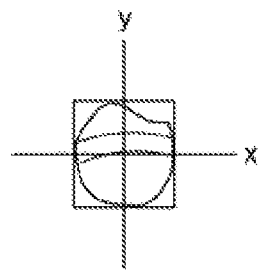
FIG. 5 is a diagram illustrating a tooth in its proper position after rotational correction.

Referring to FIG. 4, if the misaligned tooth 202 is to be rotated left, it can be seen that two points may be needed, point A on the outer side of the tooth and point B on the inner side of the tooth. As a force couple is created at the two points (point A, point B) in the desired direction of rotation, it can be seen that the tooth may be subjected to a rotational moment induced by the force couple, as illustrated in FIG. 5, to ultimately complete the rotational correction.

Figure 6:
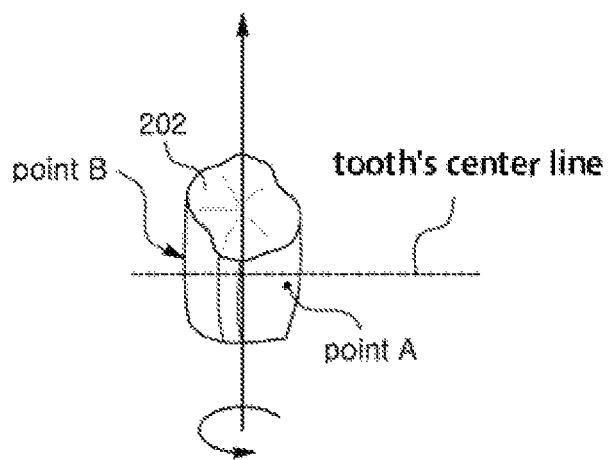
FIG. 6 represents a method of selecting the points illustrated in FIG. 4.

FIG. 6 represents a method of selecting the points illustrated in FIG. 4.

Referring to FIG. 6, it can be seen that it is more effective to choose the points such that they are lower than the center line of the misaligned tooth 202. Here, the center line of the tooth refers to an imaginary line at about the midpoint height of the misaligned tooth 202 developed upwards from the gums.

Selecting the points (point A, point B) to be higher than the center line of the misaligned tooth 202 can result in not only the force couple being generated but also a downwardly pushing force, which can hinder the rotational correction. Conversely, selecting the points (point A, point B) to be lower than the center line of the misaligned tooth 202 can result in an upward force being generated in addition to the force couple, but this upwardly pushing force would aid the rotational correction.

Here, point B may be positioned at the opposite side of point A with respect to the axis of rotation.

FIG. 7 illustrates a rotational correction model corresponding to a tooth that requires rotational correction.

Referring to FIG. 7, it can be seen that the rotational correction model 500 may have a contour portion surrounding the misaligned tooth, with two correction-position points 502, 504 formed towards the misaligned tooth so as to push the tooth in the direction in which rotation is desired. Here, the two correction-position points 502, 504 may be at positions which are symmetrical with respect to the axis of rotation and which are in contact with portions that are recessed from the tooth surface.

It may be preferable to set the positions of the two correction-position points 502, 504 of the aligner for the misaligned tooth to be lower than the middle of the misaligned tooth 202. If they are higher than the midpoint of the tooth, a pressing force that hinders the correction may be created.

FIG. 8 is a flow diagram representing a method of determining the two points illustrated in FIG. 7.

First, a tooth contour model may be determined which includes a contour that surrounds the surfaces of the tooth requiring rotational correction (s602).

The tooth contour model may have the shape of the tooth requiring rotational correction.

The axis of rotation of the tooth contour model may be determined (s604).

The axis of rotation may be determined in consideration of the geometrical shape of the tooth.

Based on the axis of rotation and the direction of rotation required for the correction, two correction-position points 502, 504 suitable for the desired direction of rotation may be determined (s606).

That is, two points may be determined which are symmetrical with respect to the axis of rotation and at which a force couple can be generated on the outer surfaces of the tooth.

A rotational correction model 500 may be determined for providing rotational correction by protruding the contour at the two points towards the inward side of the tooth and in the direction of rotation (s608).

The rotational correction model 500 may be applied to the 3D teeth alignment model data (s610).

Figure 9:
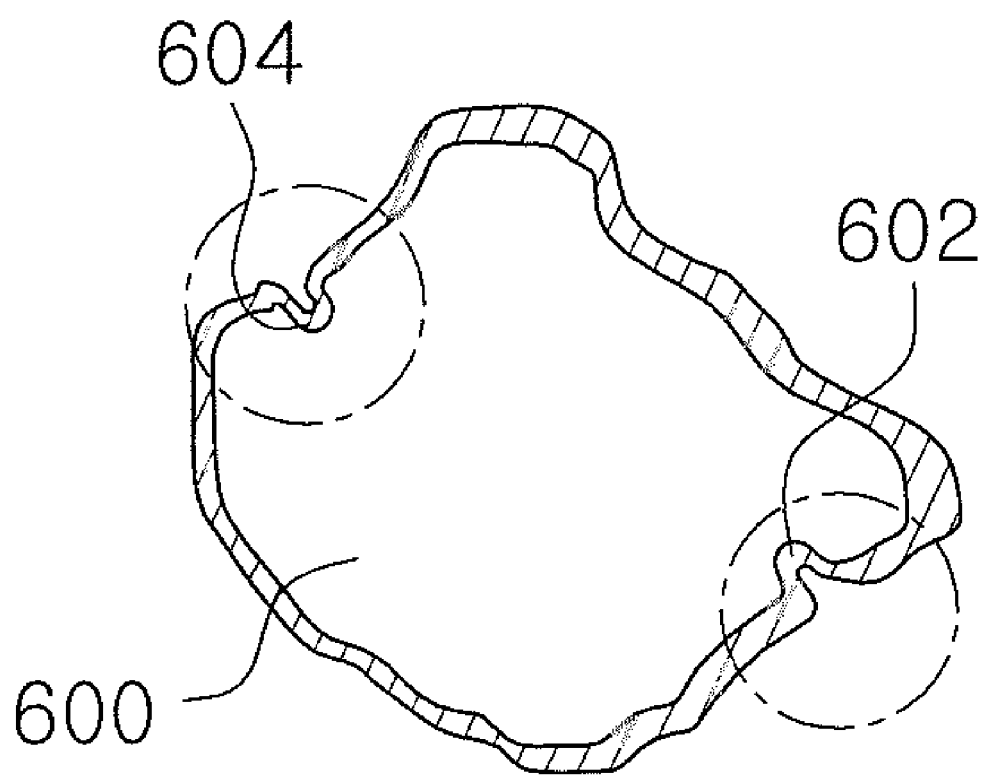
FIG. 9 illustrates a horizontal cross-section at the portion of the points chosen on an alignment tooth model.

FIG. 9 illustrates a horizontal cross-section at the portion of the points chosen on an alignment tooth model. Since the tooth contour model is shaped protruding towards the inward side of the tooth, the corresponding alignment tooth model 600 may have concave portions 602, 604 that are concave towards the inward side of the tooth.

Figure 10:
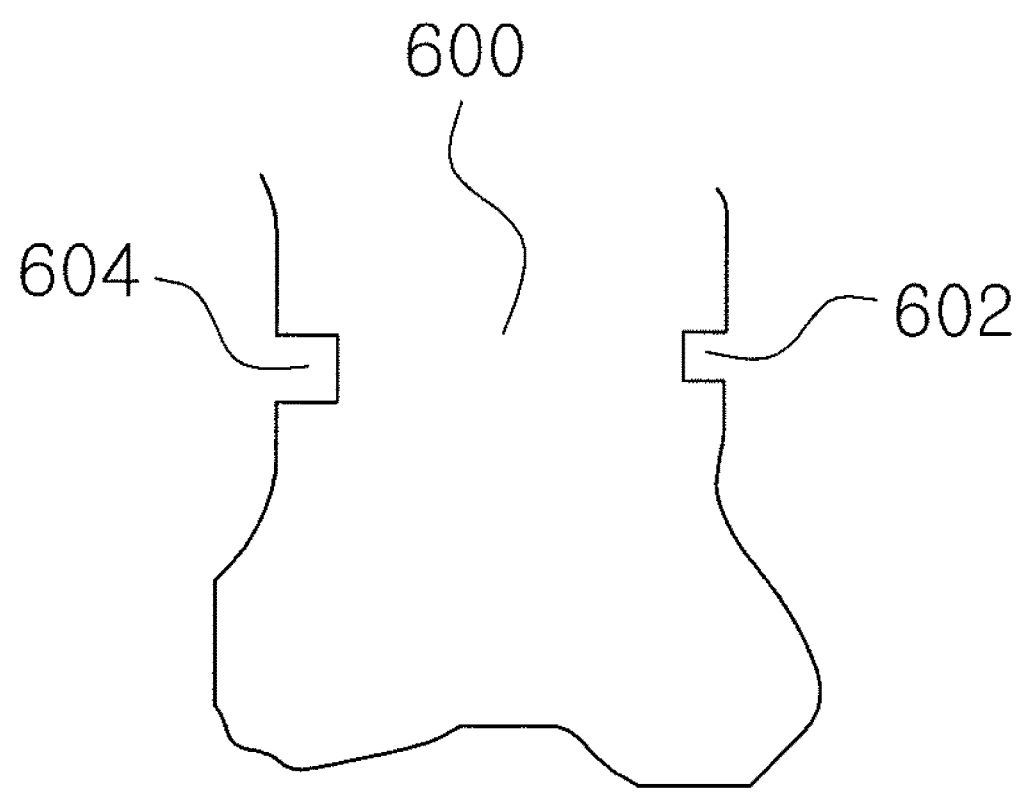
FIG. 10 illustrates a vertical cross-section at the portion of the points chosen on an alignment tooth model.

FIG. 10 illustrates a vertical cross-section for FIG. 7.

Figure 11:
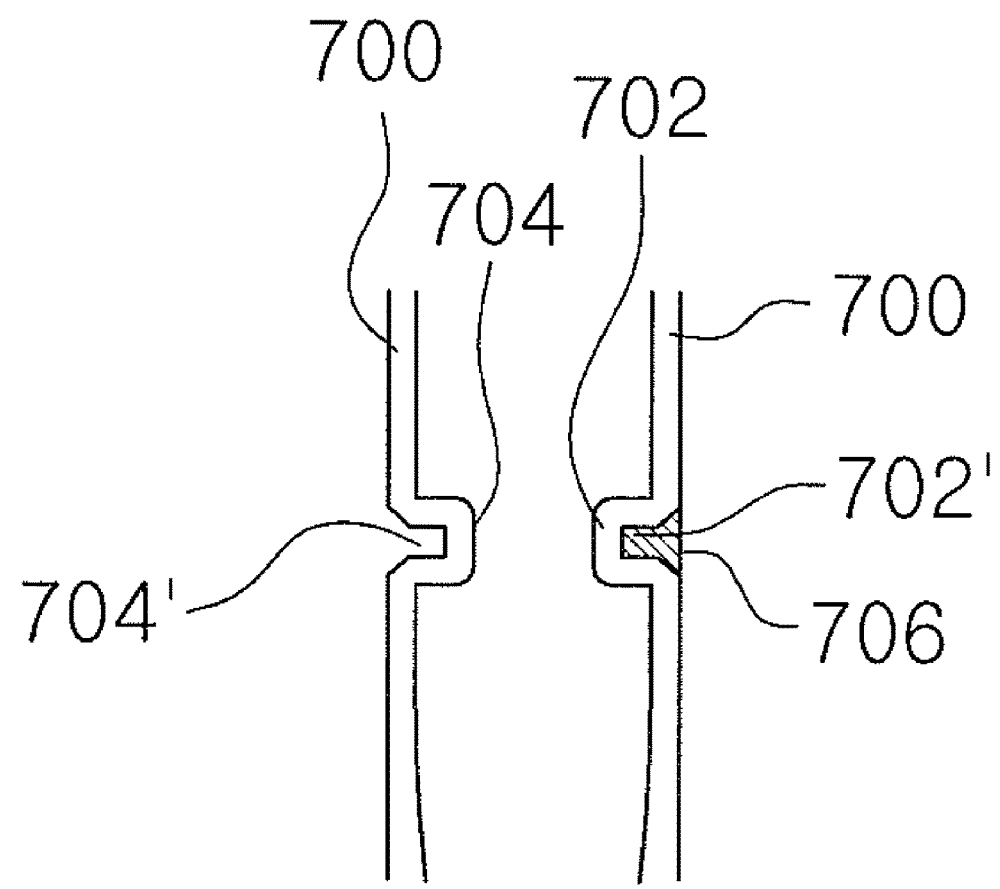
FIG. 11 illustrates the shape of a transparent aligner at the two points of an alignment model obtained from the alignment tooth model of FIG. 10.

FIG. 11 illustrates the shape of a transparent aligner obtained according to the rotational correction model of FIG. 10.

Referring to the partial magnified view of FIG. 11, the first pocket 700 of the transparent aligner may have convex portions 702, 704 formed corresponding to the two concave portions 602, 604 of the alignment tooth model 600. At the rear side of the convex portions 702, 704 of the transparent aligner, there may be formed concave portions 702', 704' of the same shape. If the concave portions 702', 704' are left empty, the convex portions 702 may not properly push the tooth because of resisting forces from the upper and lower portions of the concave portions 702', 704' and from the tooth itself.

To prevent this, the concave portions 702', 704' can be filled in with a solid support material such as resin, wax, etc. For example, a solid support 706 can be formed by filling the concave portions 702', 704' with a semisolid resin and then curing the resin. This solid support 706 may provide the convex portions 702, 704 with sufficient elasticity for properly pushing the tooth and achieving effective rotational correction. The first tooth pocket 700 may be fabricated thus to allow effective rotational correction.

Figure 12:
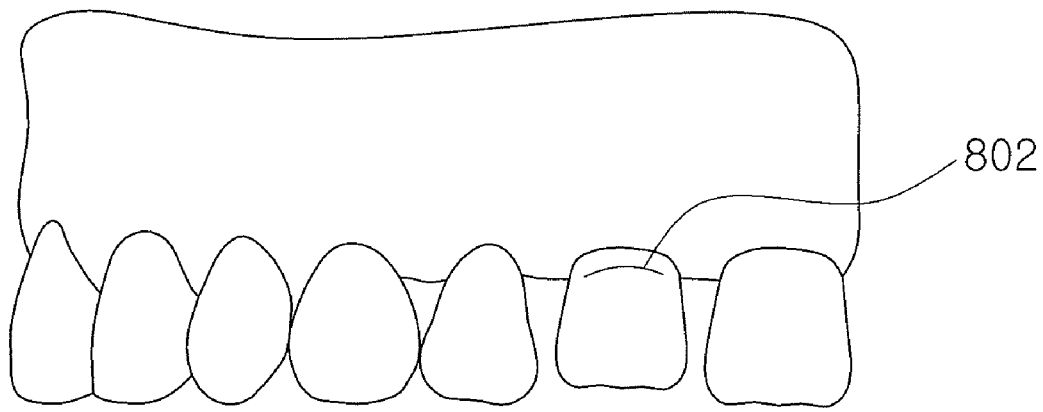
FIG. 12 is a diagram for explaining an alignment teeth model according to a second embodiment of the present invention for a tooth that is smaller in size than other teeth and requires slight pulling to match the sizes of the other teeth.

FIG. 12 is a diagram for explaining a method of manufacturing a transparent aligner according to another embodiment of the present invention and is provided to illustrate a method of correcting a tooth that requires pulling aid.

Figure 13:
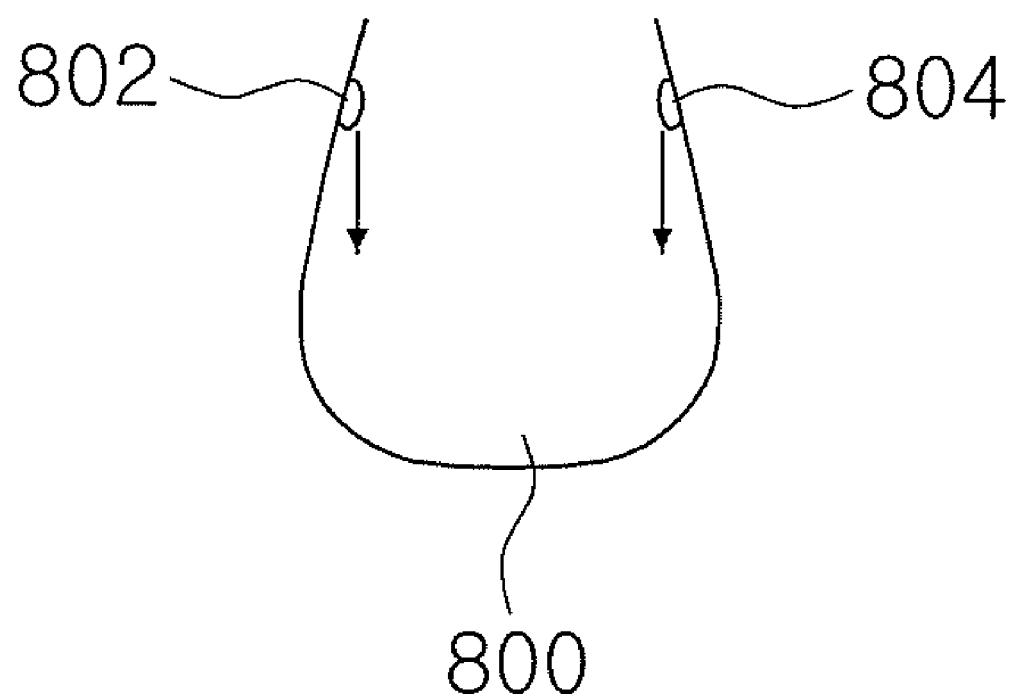
FIG. 13 illustrates an aligner based on the second embodiment considered in connection with the manufacture of the transparent aligner of FIG. 12.

The method illustrated in FIG. 12 is for forming a second tooth pocket 800. In FIG. 13, an example is illustrated which includes second convex portions 802, 804 protruding from the labial side and lingual side of a tooth requiring pulling aid.

That is, in the inner walls of a second tooth pocket, which corresponds to a tooth that is developing slower than or has a smaller size than the other teeth and hence requires pulling aid, there may be pulling-aid protrusions that are the second convex portions 802, 804 formed at the lingual side and labial side of the tooth by protruding upward or downward to help pull the tooth.

Such a second tooth pocket 800 can be determined during the process of generating an alignment teeth model (s104) in FIG. 1. That is, a second tooth pocket 800 for a pulling-correction aligner having the second convex portions 802, 804 as the pulling-aid protrusions can be formed by forming an alignment teeth mockup to which the second tooth pocket 800 of the transparent aligner having the second convex portions 802, 804 as the pulling-aid protrusions has been applied, and then placing a synthetic resin fabric thereon and applying vacuum compression.

More specifically, similar to the case of the tooth requiring rotational correction, a tooth contour model may be determined that has a contour portion surrounding the surfaces of a tooth requiring pulling aid.

The following description references FIG. 13.

In the tooth contour model, two points may be determined where forces may be applied to push the tooth requiring pulling aid in the direction of pulling.

A pulling correction model may be determined by forming protrusions at the two points, where the contour portion of the tooth contour model protrudes in the direction of pulling.

The pulling correction model thus determined may be applied to the 3D alignment teeth model.

Figure 14:
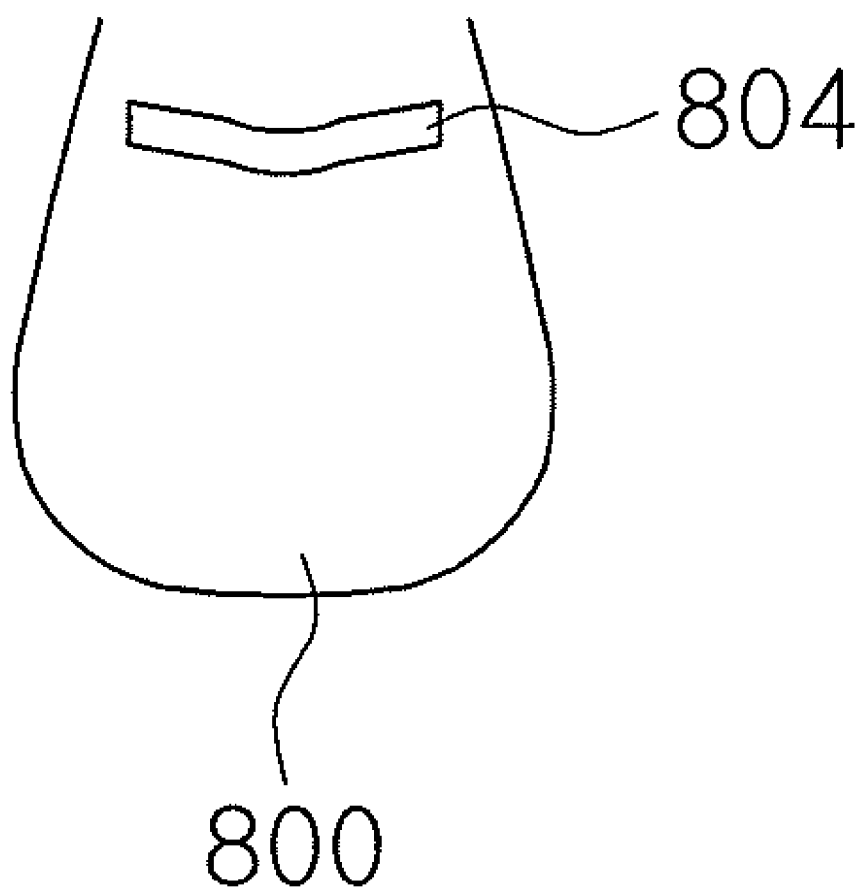
FIG. 14 illustrates the aligner of FIG. 13 as seen from the left or right side.

As illustrated in FIG. 14, the pulling-aid protrusions may extend along a horizontal direction of the tooth requiring pulling aid and may preferably have a "U" shape with the concave part facing the direction of pulling.

Returning to FIG. 1, a 3D printer may be used to fabricate an alignment teeth mockup (s106).

Figure 15:
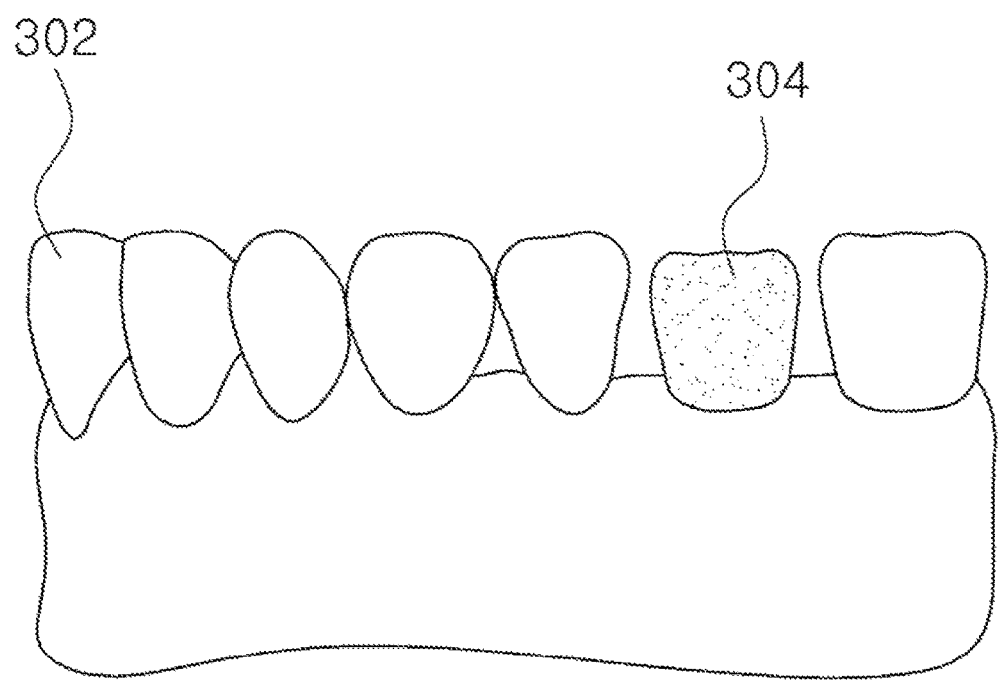
FIG. 15 is a diagram for explaining an alignment teeth model according to a third embodiment of the present invention in which a wax or resin mold is provided at a position corresponding to where a permanent tooth will develop for cases in which a permanent tooth is as yet missing.

FIG. 15 is a diagram for illustrating a method of manufacturing a transparent aligner according to still another embodiment of the present invention. In FIG. 15, an example is illustrated which includes a tooth pocket (third pocket) corresponding to a part where a permanent tooth will develop after a primary tooth has been shed.

Referring to FIG. 15, a mold 304 of wax or resin can be provided in the alignment teeth mockup 302 at a position where a primary tooth has been shed and a permanent tooth has not yet developed, in the case of an adolescent, or where a permanent tooth is missing, in the case of an adult. Here, the shape of the mold can assume the shape of a developed permanent tooth.

By performing the vacuum compression with synthetic resin fabric placed over the alignment teeth mockup 302 after thus molding and curing a mold 304 made of wax or resin in the shape of a permanent tooth, it is possible to form a third tooth pocket corresponding to a part where a primary tooth has been shed.

Figure 16:
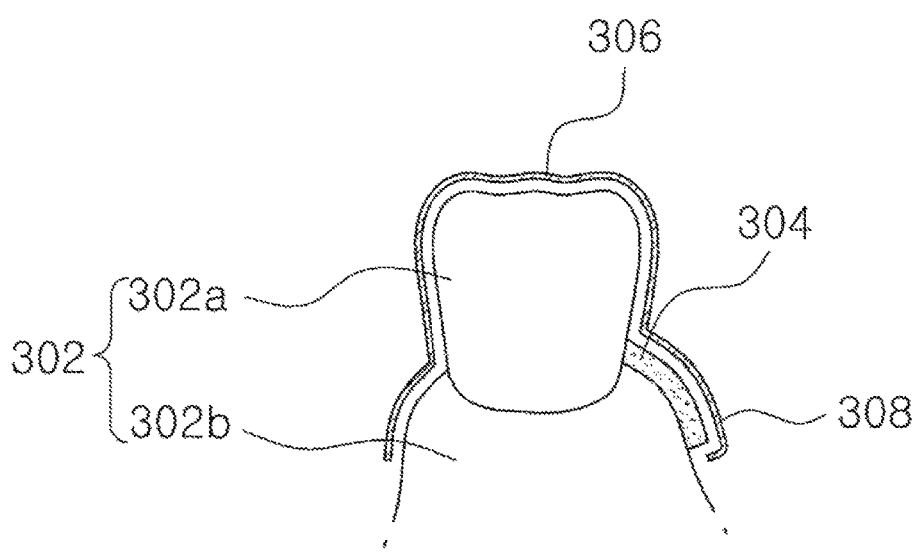
FIG. 16 is a diagram for describing a method for manufacturing a transparent aligner according to a fourth embodiment of the present invention.

FIG. 16 is a diagram for describing a method for manufacturing a transparent aligner according to a yet another embodiment of the present invention. In FIG. 16, an example is provided in which a handle part is formed to enable easy removal of the transparent aligner.

Numeral 302a represents a tooth on an alignment teeth mockup, while numeral 302b represents a gum portion on the alignment teeth mockup.

To be more specific, an elliptical patch 306 may be attached at the outside gum portion at each of an upper and a lower molar of the alignment teeth mockup.

The elliptical patch 306 is for forming a handle 308 that will be located at a lower portion of a molar on the transparent aligner, and its shape may be the same as the contour of the handle 308. That is, the elliptical patch 306 may extend from a lower end of the gum to the boundary between the gum and the tooth, and its thickness and width may preferably be of such a degree that allows entry by the end part of a finger nail.

The transparent aligner may thus be manufactured using an alignment teeth mockup with the elliptical patch 306 attached.

By performing the vacuum compression with synthetic resin fabric placed over the alignment teeth mockup 302 with an elliptical patch 306 attached thus, it is possible to form the transparent aligner with a handle 308 formed at the portion corresponding to the elliptical patch 306.

The operation of generating the 3D dental alignment model data may entail dividing into several stages and creating mockups based on a simulation of the several stages using a program until the desired alignment teeth mockup is completed.

Also, in order to obtain the desired alignment teeth mockup, it may be preferable to create teeth models of different shapes by outputting fixed teeth mockups set for the various stages.

Using several transparent aligners created from sequential teeth models may enable a wearer to freely and painlessly take off and reapply an aligner, providing the advantages of increased freedom and effectiveness in the dental alignment.

Figure 17:
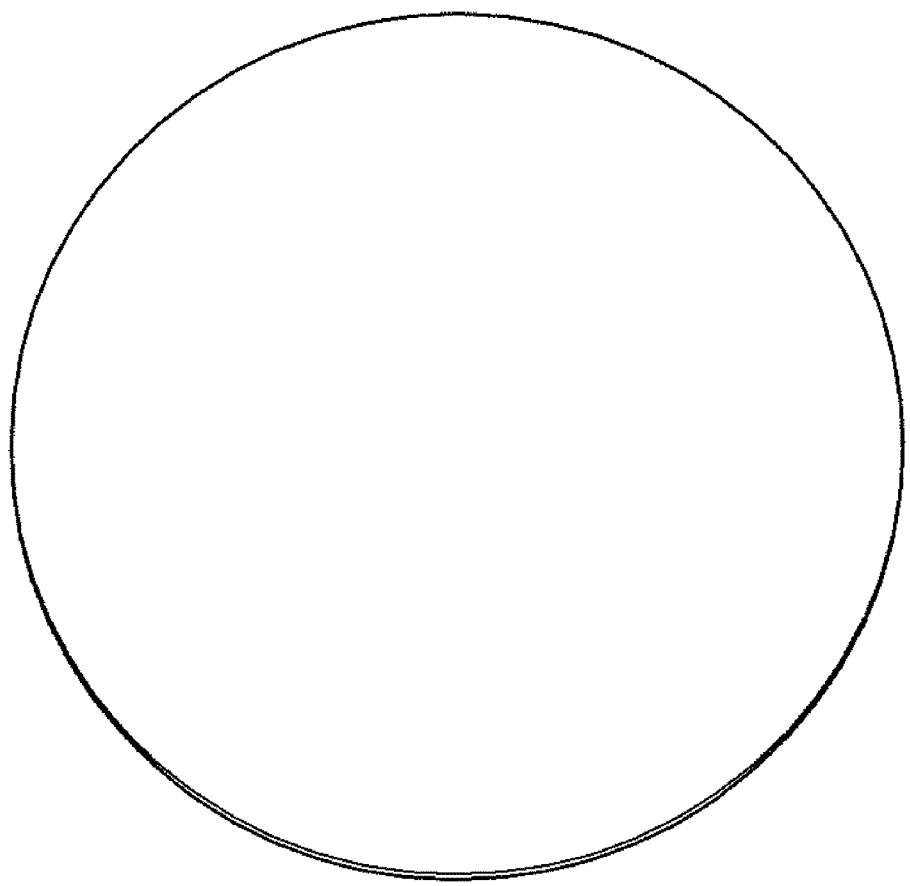
FIG. 17 illustrates an example of a heat seal resin.
Figure 18:
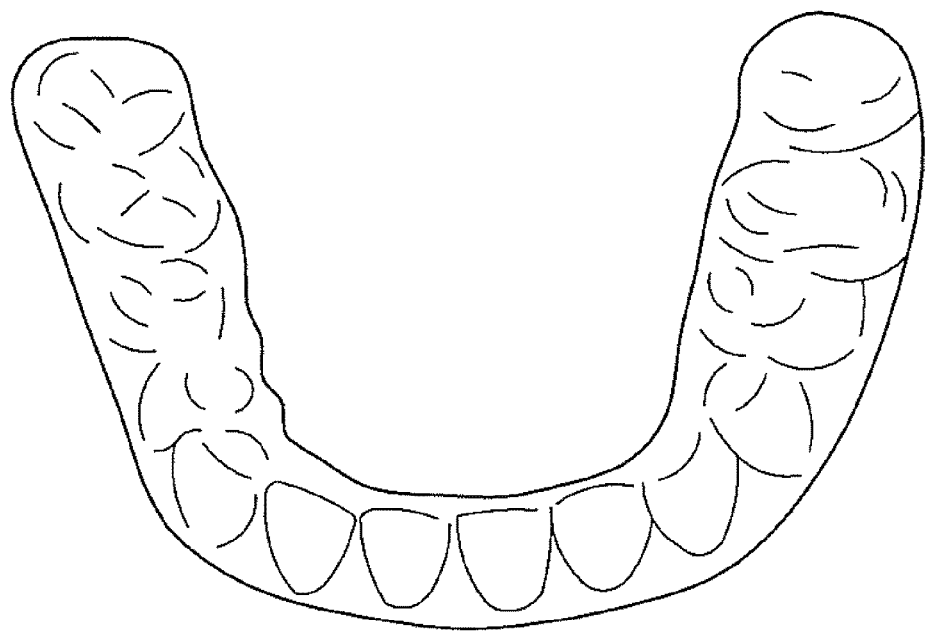
FIG. 18 illustrates a cover that has the same shape as a transparent aligner and is made from the heat seal resin of FIG. 17.

Onto an alignment teeth mockup 302 that includes any one of or a combination of a first tooth pocket, a second tooth pocket, a third tooth pocket, and an elliptical patch, a heat seal resin such as that illustrated in FIG. 17 may be applied and heated to obtain a cover such as that illustrated in FIG. 18.

This cover may be applied to allow easier separation between the alignment teeth model and the transparent aligner when applying the synthetic resin to manufacture the transparent aligner.

Figure 19:
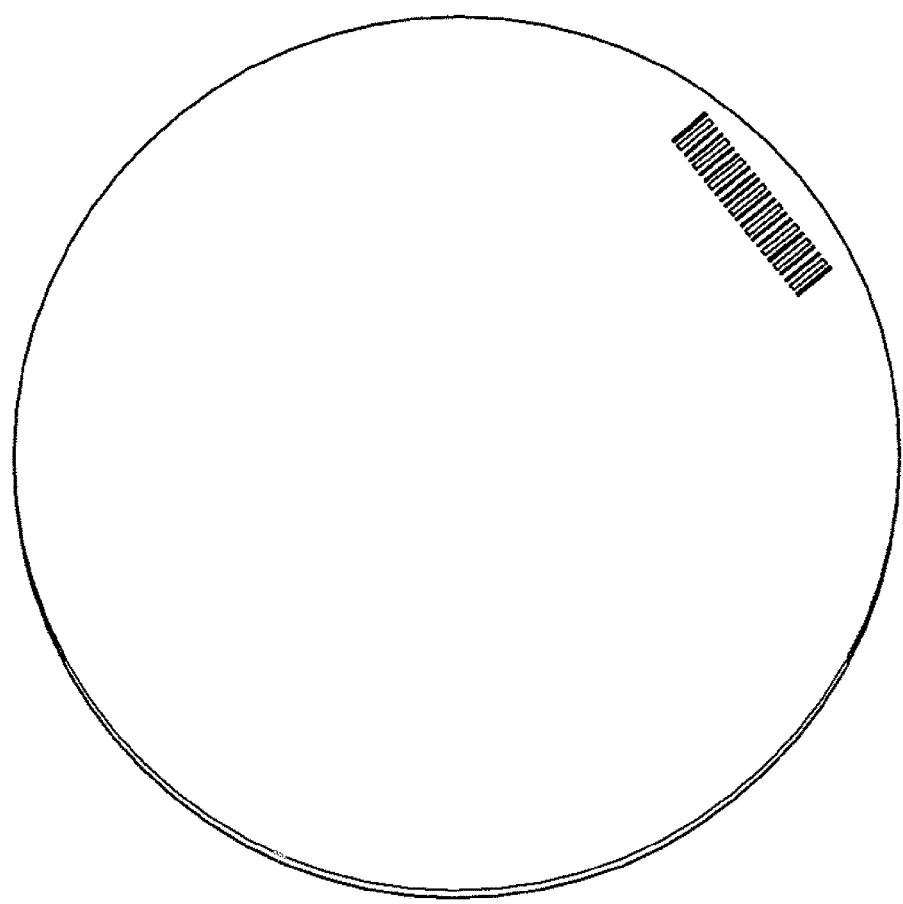
FIG. 19 illustrates an example of a synthetic resin.
Figure 20:
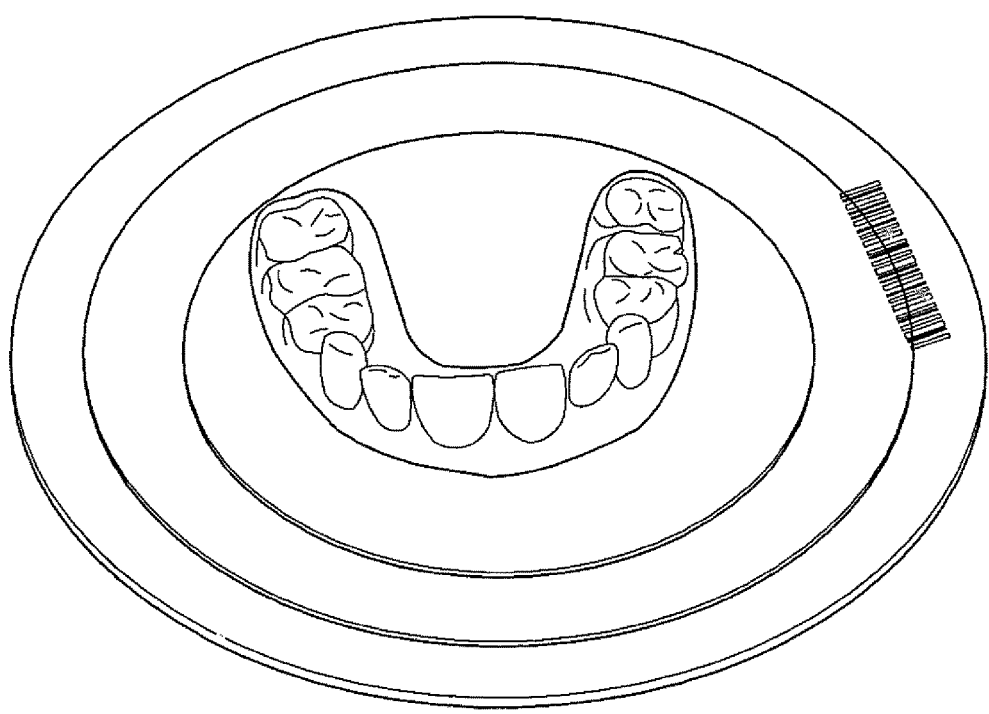
FIG. 20 illustrates an example of a mold.

A synthetic resin fabric such as that illustrated in FIG. 19 may be applied over an alignment teeth mockup after the cover has been placed thereon, and then by performing vacuum compression, a mold such as that illustrated in FIG. 20 may be obtained. Then, the concave portions 702', 704' of a first tooth pocket corresponding to a tooth requiring rotational correction may be filled with a resin, and the resin may be cured to form solid supports 706.

Here, synthetic resin sheets of different thicknesses may be applied to obtain a set of molds. For example, four sheets having thicknesses of 0.02 inches, 0.03 inches, 0.035 inches, and 0.004 inches, for example, can be applied to obtain a collection of molds having four different thicknesses from the same alignment teeth mockup.

Figure 21:
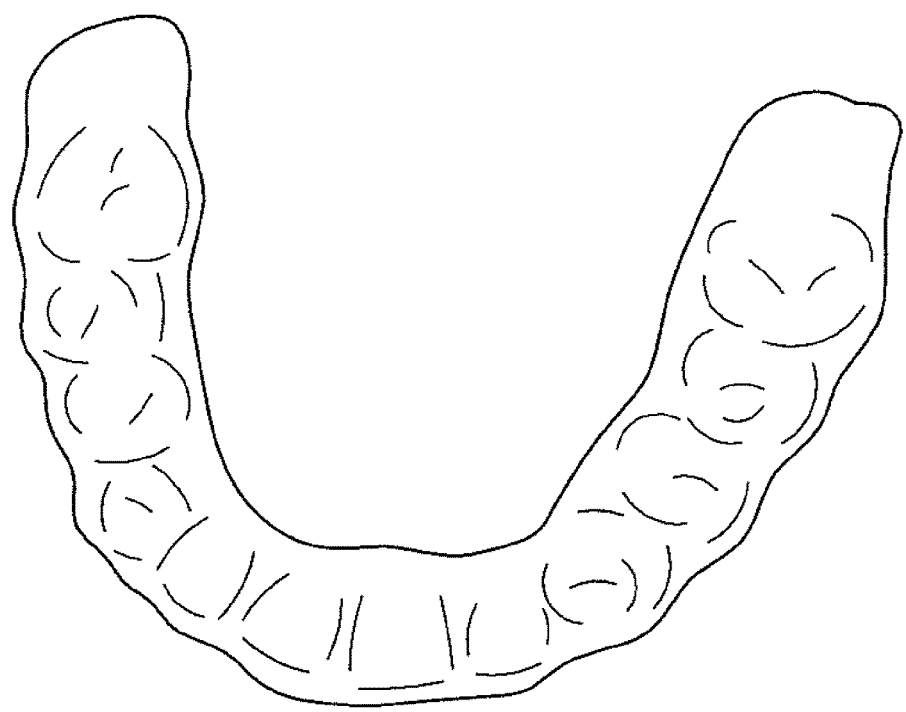
FIG. 21 illustrates a transparent aligner.

The molds illustrated in FIG. 20 may be tailored to provide a collection of transparent aligners composed of several transparent aligners having different thicknesses, such as that illustrated in FIG. 21, applied for the alignment treatment.

Figure 22:
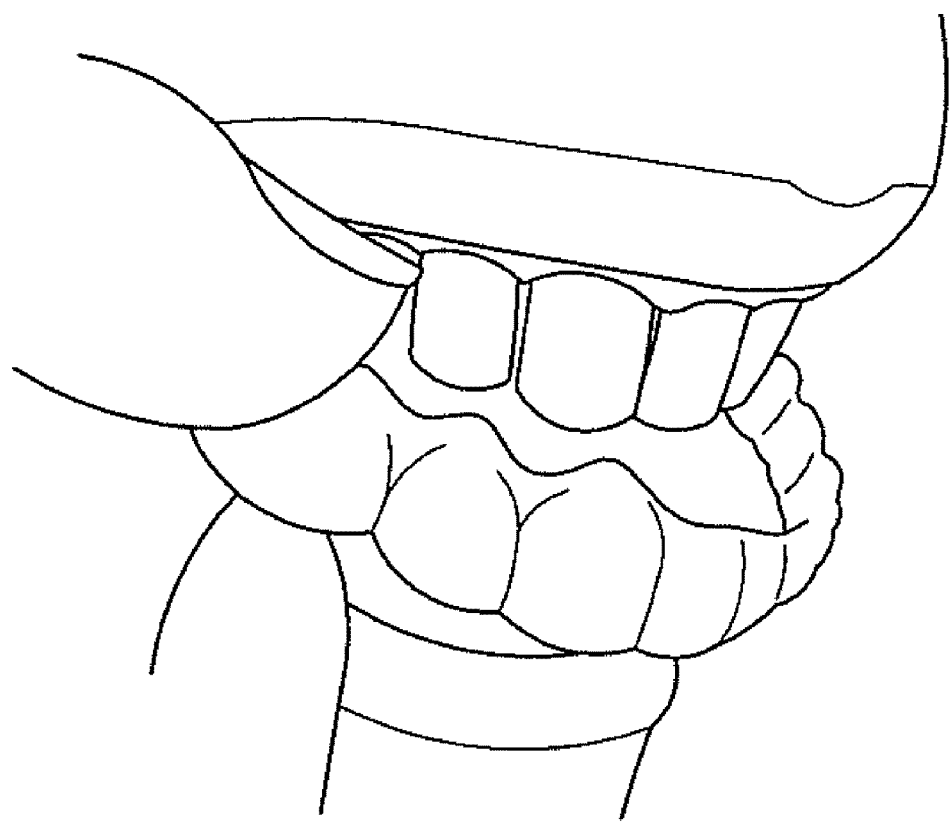
FIG. 22 illustrates an example of putting on a transparent aligner.
Figure 23:
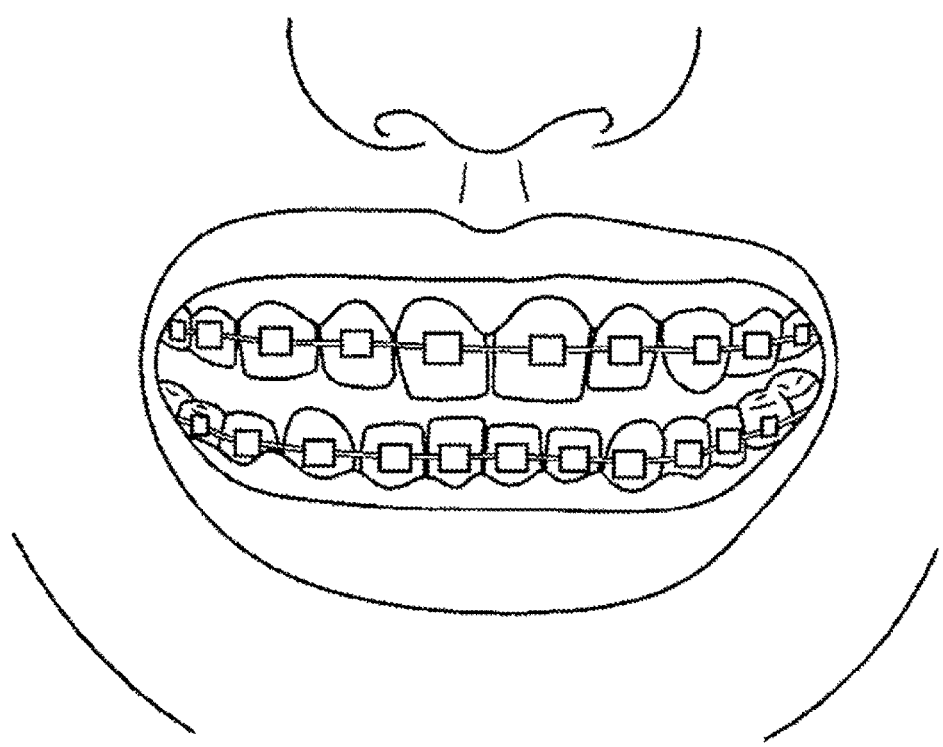
FIG. 23 illustrates an example of a fixed aligner according to the related art as worn by a patient.

FIG. 22 illustrates a way of putting on the transparent aligner.

With the transparent aligners according to an embodiment of the present invention, a wearer may wear the transparent aligners having four thicknesses, one for each week. This would incur relatively less pain, even when the distances moved by the teeth are great, and since the aligner can be replaced each week, any discoloring of the teeth or bad breath, etc., caused by contamination of the aligner can be prevented. Also, since abrasion of the aligner may be avoided, the alignment can be performed with greater precision.

The descriptions set forth above serve merely as examples based on the technical spirit of the present invention. A person skilled in the art would be able to utilize these examples to provide various modifications without departing from the technical spirit of the present invention as expressed by the scope of claims.

INDUSTRIAL APPLICABILITY

The present invention offers industrial applicability in that it provides not only a method for manufacturing a transparent aligner that enables easy and effective rotational correction and removal but also a method for manufacturing a transparent aligner which can provide an allowance space for a permanent tooth before or after a primary tooth is shed and with which different thicknesses can be used to adjust the duration of the aligning.

The invention claimed is:
1. A method for manufacturing a transparent dental aligner, the transparent dental aligner comprising: an insertion aligner part and a support part, the insertion aligner part having tooth pockets formed therein corresponding to an aligned teeth arrangement, the insertion aligner part configured to be fitted over a corresponding group of teeth, and the support part extending from the insertion aligner part to a gum, the method comprising:
- providing a 3D-modeled teeth mockup;
- generating 3D dental alignment model data by incorporating alignment data into the 3D-modeled teeth mockup;
- fabricating an alignment teeth mockup using the 3D dental alignment model data; and
- applying vacuum compression after placing a synthetic resin sheet on the alignment teeth mockup,
- wherein the generating of the 3D dental alignment model data comprises:
- determining a tooth contour model, the tooth contour model having a contour portion surrounding a surface of a tooth requiring rotational correction;
- determining an axis of rotation for the tooth requiring rotational correction;
- determining two points touching exterior surfaces of the tooth requiring rotational correction based on the axis of rotation and a direction of rotation required for correcting the tooth requiring rotational correction, the two points being symmetrical with respect to the axis of rotation;
- determining a rotational correction model for the rotational correction by protruding the contour portion towards a tooth surface and towards a direction of rotation at the two points; and
- generating the 3D dental alignment model data by applying the rotational correction model.

2. The method for manufacturing a transparent dental aligner according to claim 1, further comprising:
- determining a tooth contour model, the tooth contour model having a contour portion surrounding a surface of a tooth requiring pulling aid;
- determining a point for creating a force pushing the tooth requiring pulling aid in a direction of pulling, at each of a labial side and a lingual side of the tooth requiring pulling aid; and
- determining a pulling correction model for the pulling correction by protruding the contour portion towards a direction of pulling at the two points.

3. The method for manufacturing a transparent dental aligner according to claim 1, further comprising, before the applying of the vacuum compression:
- attaching an elliptical patch at an outside gum portion at a molar of the alignment teeth mockup.

4. The method for manufacturing a transparent dental aligner according to claim 1, further comprising, before the applying of the vacuum compression:
- molding a resin in accordance to a shape of a permanent tooth at a tooth portion of the alignment teeth mockup where a primary tooth was shed and a permanent tooth has not yet developed; and
- curing the resin.

5. The method for manufacturing a transparent dental aligner according to claim 1, wherein the applying of the vacuum compression comprises sequentially applying synthetic resin sheets of different thicknesses to fabricate a plurality of transparent dental aligners.

6. The method for manufacturing a transparent dental aligner according to claim 1, wherein a heat seal resin is applied on the alignment teeth mockup to provide a cover before the applying of the vacuum compression, and the applying of the vacuum compression is performed with the obtained cover covering the alignment teeth mockup.

7. The method for manufacturing a transparent dental aligner according to claim 1, wherein the generating of the 3D dental alignment model data comprises generating mockups of several stages based on a simulation of several stages using a program until a desired teeth mockup is completed.

8. The method for manufacturing a transparent dental aligner according to claim 1, wherein teeth models of several shapes are created by outputting teeth mockups set according to several stages in order to obtain a desired teeth mockup.

* * * * *